United States Patent [19]

Venburg et al.

[11] Patent Number: 5,801,119

[45] Date of Patent: Sep. 1, 1998

[54] PROCESS FOR INHIBITING STEM ELONGATION IN BULBOUS PLANTS AND CUT FLOWERS THEREFROM

[75] Inventors: Gregory D. Venburg, Deerfield; James R. Hansen, Palatine; Derek D. Woolard, Waukegan; Warren E. Shafer; Candace Black-Schaefer, both of Libertyville, all of Ill.

[73] Assignee: Abbott Laboratories, Abbott Park, Ill.

[21] Appl. No.: 775,467

[22] Filed: Dec. 31, 1996

[51] Int. Cl.$^6$ .................................................. A01N 37/44
[52] U.S. Cl. ........................... 504/115; 504/319; 504/320
[58] Field of Search ............................. 504/115, 319, 504/320

[56] References Cited

U.S. PATENT DOCUMENTS

| | | | |
|---|---|---|---|
| 4,441,918 | 4/1984 | Rehberg | 71/113 |
| 5,284,818 | 2/1994 | Shafer et al. | 504/115 |
| 5,500,403 | 3/1996 | Shafer et al. | 504/115 |
| 5,523,281 | 6/1996 | Shafer et al. | 504/320 |

OTHER PUBLICATIONS

A–Rest® Solution Product Information from Elanco Products Company (1987).
Bonzi® Ornamental Growth Regulator Product Information from Uniroyal Chemical (1995).
Cerone® Plant Regulator Product Information from Crop Protection Chemicals Reference, 10th ed., Chemical and Pharmaceutical Press, New York, pp. 984–986, (1994).
Ethrel® Ethepon Plant Regulator Product Information from Rhone–Poulenc Ag Company, pp. 1423–1430 (1993).
Florel® Plant Growth Regulator Product Information from Lawn and Products, Inc. (1994).
Baker, J.E., et al., *HortScience* 12(1): 38–39 (1977).
Beyer, E.M., et al., in *Advanced Plant Physiology*, Wilkens, M.G., ed., Longman Scientific and Technical, Essex, U.K., pp. 111–126 (1984).
De Hertogh, A., *Holland Bulb Forcers Guide*, 4th ed. pp. B–5–B–7 & C–44 (1989).
Dettertogh, A., and M. Le Nard, eds., *The Physiology of Flower Bulbs*, Elsevier, Amsterdam, pp. 7, 19–20, 21, 38, 42–43, 619–621, 660, 673–682 (1993).
Gussman, C.D., et al., *Plant Growth Regulation*, 12:149–154 (1993).
Halevy, A.H., et al., *Horticultural Reviews*, 3:59–143 (1981).
International Floriculture Trade Statistics 1991, Pathfast Publishing Essex, U.K., pp. 8, 9, 75 and 98.
Kamerbeek, G.A., et al., *Scientia Horticulture*, 4: 101–115 (1976).
Kanneworff, W.A., et al., *J. Plant Physiol.*, 143:200–206 (1994).
Moe, R., *Acta Horticulturae*, 109:197–204 (1980).
Norcini, J.A., et al., *HortTechnology*, 6(3): 207–210 (Jul./Sep. 1996).
Rademacher, W., in *Plant Biochemical Regulators*, H.W. Gausman, ed., Marcel Dekker, New York, pp. 169–200 (1991).
Sacalis, J.N., *Cut Flowers, Prolonging Freshness*, Seals, J.L., ed., 2nd ed. Ball Publishing pp. 101–102 (1993).
Voigt, A.O., *Flora & Nursery Times*, 2:52&55 (Dec. 1995).
Wang, C.Y., et al., *HortScience* 15(6):805–806 (1980).
Wees, D., *Can. J. Plant Sci.*, 73:879–883 (Jul. 1993).
Yang, S.F., et al., *Ann. Rev. Plant Physiol.*, 35:155–189 (1984).

*Primary Examiner*—S. Mark Clardy
*Attorney, Agent, or Firm*—Lawrence S. Pope

[57] ABSTRACT

A process of inhibiting stem elongation in ornamental bulbous plants or in cut flowers from such plants, involving treating such plants or flowers with an effective amount of ACC synthase inhibitor, such as aminoethoxyvinylglycine and aminooxyacetic acid to inhibit stem elongation, by administration of a solid, semi-solid or a solution of such ACC synthase inhibitor.

10 Claims, No Drawings

PROCESS FOR INHIBITING STEM ELONGATION IN BULBOUS PLANTS AND CUT FLOWERS THEREFROM

TECHNICAL FIELD

This invention relates to a process for inhibiting stem elongation in ornamental flowering bulbous plants and cut flowers from such plants. More specifically, the present invention involves inhibiting stem elongation by administering to a bulbous plant or cut flowers from such plants, a sufficient amount of an ACC synthase inhibitor to accomplish such purpose.

BACKGROUND OF THE INVENTION

The production and trade of ornamental flowering plants and cut flowers is a significant business worldwide. For example, in 1990 the consumption of cut flowers and flowering plants at the retail level in the United States was estimated at 8.697 billion U.S. dollars (International Floriculture Trade Statistics 1991, Pathfast Publishing, Essex, UK, pg. 98). The consumption of cut flowers and flowering plants in 15 nations (including Western Europe, Japan, and the U.S.A.) in 1990 was estimated at 16.611 billion U.S. Dollars (Ibid.).

Bulbous plants are plant species characterized by specialized underground organs which store food and moisture thereby allowing for seasonal growth and development (De Hertogh, A. and M. Le Nard, eds., The Physiology of Flower Bulbs, Elsevier, Amsterdam, p. 7 (1993)). Bulbous plants include acidanthera, agapanthus, allium, alstroemeria, amaryllis, anemome, astilbe, begonia, caladium, canna, chionodoxa, convallaria, crocosmia (montebretia), crocus, cyclamen, dahlia, daffodil, endymion, eranthis, eremurus, freesia, fritillaria, gladiolus, hyacinth, iris, ixia, liatris, lily, muscari, nerine, ornithogalum, polianth, ranunculus, scilla, triteleia, tulip and zantedeschia (calla lily). The most important genera are Gladiolus, Hyancinthyus, Iris, Lilium, Narciscuss (daffodil), and Tulipa. These genera are each produced on an excess of 900 hectares and represent about 90% of the world's flower bulb production acreage (Ibid., p. 21).

The worldwide flower bulb production area is estimated at over 32,000 hectares. The Netherlands is the largest producer with about 55% of the reported production area (Ibid.). The major flower bulb is the tulip and the Netherlands is the predominant tulip bulb grower. In the 1989–90 growing season, the Dutch produced 2.777 billion tulip bulbs. In that year, the Netherlands produced approximately 900 million cut tulip flower stems (Ibid., pp. 619–621). The value of exports of cut tulips from the Netherlands in 1990 was reported at 143.6 million U.S. dollars (International Floriculture Trade Statistics, Pathfast Publishing, Essex, U.K., p. 75 (1991)).

One of the problems often associated with bulbous plants is excessive stem elongation. With potted bulbous plants, it is desirable to inhibit stem elongation in order to produce compact plants which are preferred by consumers. With cut tulips, the stems continue to grow after harvesting, curving towards the light. This uneven stem elongation can significantly detract from the attractiveness of cut tulip flowers and thereby reduce their effective vase life. Cut flower preservatives tend to exacerbate this stem elongation and consequently are therefore not recommended for cut tulips (Sacalis, J. N., Cut Flowers, 2nd ed. Ball Publishing, Batavia, Ill., pp. 101–102 (1993)).

Ethylene is a gaseous plant hormone that is involved in the modulation of a number of plant biochemical pathways. Ethylene affects such processes as abscission, flowering, seed germination, sex expression, root growth, internode elongation, epinasty, ripening, fruit set, senescence, and geotropism. (Beyer, E. M., Morgan, P. W., Yang, S. F. In Advanced Plant Physiology, Wilkens, M. G. ed., Longman Scientific and Technical, Essex, U.K., pp. 111–126 (1984)). Plants produce ethylene by converting methionine present in the plants to S-adenosylmethionine (known by the acronym "SAM"), then to 1-aminocyclopropane-1-carboxylic acid (known by the acronym "ACC") and finally to ethylene. The key regulatory step in the ethylene biosynthesis pathway is the conversion of SAM to ACC which is regulated by the enzyme ACC synthase (Ibid.). The activity of ACC synthase is known to be inhibited by substances such as L-trans-2-amino-4-(2-aminoethoxy))-3-butenoic acid (also known by the common name aminoethoxyvinylglycine and the acronym "AVG") and carboxymethoxylamine (also known by the common name aminooxyacetic acid and the acronym "AOA") (Ibid.; and Yang, S. G., Hoffman, N. E., Ann. Rev. Plant Physiol., 35:155–189 (1984)). AVG and AOA are competitive inhibitors of ACC synthase.

In bulbous plants, ethylene influences a number of developmental processes. For example, in small iris bulbs, exposure to low concentrations of ethylene leads to flower formation (Kanneworff, W. A., et al., J. Plant Physiol. 143:200–206 (1994)). Without ethylene exposure, these bulbs would produce only three long leaves and no flowers (Ibid.). Also, ethylene has been found to inhibit the elongation and growth of shoots and roots in potted iris, narcissus, tulip and hyacinth plants (Kamerbeek, G. A., et al., Scientia Horticulturae 4:101–115 (1976)).

In a number of bulbous plants, ethylene can also cause many physiological disorders. It is known, for example, that tulips are very sensitive to ethylene during storage, transport, and at the early stages of development in the greenhouse (Moe, R., Acta Horticulturae 109:197–204 (1980)). In addition, ethylene is also known to cause gummosis, bud necrosis and flower blasting in potted tulips (Kanneworff, W. A., et al., J. Plant Physiol. 143:200–206 (1994)).

Ethylene is known to reduce the vase life of cut flowers of many bulb plants, including lilies and tulips (Sacalis, J. N., Cut Flowers, 2nd ed. Ball Publishing, Batavia, Ill., pp. 101–102 (1993)). Ethylene also causes gummosis in hyacinths and irises. In lilies, hyacinths and irises, ethylene can evoke or stimulate abscission of the flower buds (Ibid.)

Plant growth regulators (PGR's) which suppress plant growth are used commercially on a wide variety of crops, including flowering ornamental plants.

PGR's that retard plant growth can be separated into three major groups based upon their biochemical mode of action: inhibitors of gibberellin (GA) biosynthesis, inhibitors of GA translocation, and ethylene-releasing compounds (Rademacher, W. in H. W. Gausman, ed., Plant Biochemical Regulators, Marcel Dekker, N.Y., pp. 169–200 (1991)). Gibberellins are endogenous plant hormones and one of their major effects is elongation of shoots. By inhibiting a step(s) in the GA biosynthetic pathway, the formation of the GA's is prevented and plant growth is subsequently retarded. Common examples of growth retardants that act by inhibition of GA biosynthesis are chlormequat chloride, mepiquat chloride, ancymidol, paclobutrazol, and cimectacarb. Chlormequat chloride and mepiquat chloride inhibit the early steps of GA biosynthesis and prevent the formation of the GA precursor ent-kaurene. Ancymidol and paclobutrazol inhibit the oxidation of ent-kaurene to the GA precursor ent-kaurenoic acid. Cimectacarb inhibits the later steps of GA biosynthesis. A second group of growth retardants inhibit GA translocation. An example of a growth retardant in this class is daminozide. By inhibiting the translocation of GAs or GA precursors to the sites of active growth within a plant, shoot growth can be retarded. In addition to inhibiting GA translocation, it has been suggested that daminozide may also promote the inactivation of GAs (Ibid.). Daminozide has a broad range of effects on plants, including increasing fruit set as well as of inhibiting plant growth. It has also been reported that in apples, daminozide can inhibit ethylene production (Gussman, C. D., S. Salas and T. J. Gianfagna, Plant Growth Regulation, 12:149–154 (1993)). However, unlike specific inhibitors of ACC synthase, daminozide does not appear to be a competitive inhibitor of ACC synthase. For example, unlike an ACC synthase inhibitor, daminozide has no effect on ethylene production when added to apple tissue discs (Ibid.). The third group of plant growth retardants are compounds that release ethylene. Ethephon is a compound which decomposes in plants following application to form ethylene once applied to plants. Ethylene can affect a number of processes in plants, including inhibiting stem elongation.

Three commonly used PGRs for controlling plant height in bulbous plants are ancymidol, paclobutrazol, and ethephon.

Ancymidol (alpha-cyclopropyl-alpha-(p-methoxyphenyl) 5-pyrimidine methanol) is known commercially as A-Rest®. Ancymidol is approved by the U.S. Environmental Protection Agency (EPA) for use on tulips, chrysanthemums, poinsettias, Easter lilies, and potted dahlias. Ancymidol is applied to plants as either a foliar spray or a soil drench. However, for use with potted tulips, the only effective method of application is by soil drench.

While ancymidol does reduce internode (stem) elongation in various plants, it can cause chlorosis of lower leaves (Wees, D., Can. J. Plant Sci., 73:879–883 (July 1993)). Furthermore, application of ancymidol to a plant must be made carefully. Overdosing application or uneven application of ancymidol will result in excessive or irregular growth control.

A second commonly-used plant growth retardant for bulb plants is paclobutrazol ((±)-(R,R)-beta((4-chlorophenyl) methyl)-alpha-(1,1-dimethylethyl)-1H-1,2,4-triazole-1-ethanol). Paclobutrazol is known commercially as Bonzi®. Paclobutrazol can be used for height control in various plants and can be applied as a foliar spray, soil drench, or bulb soak. When paclobutrazol is applied as a foliar spray, the spray must not be applied to the point of excessive runoff into the potting media. Too much runoff into the media may result in excessive height control. Furthermore, the foliar spray must be applied to the plant in a thorough, consistent, and uniform manner. Failure to do so may result in non-uniform height control. Also, the persistence of paclobutrazol in the soil can be a potential problem (De Hertogh, A. and M. Le Nard, eds., The Physiology of Flower Bulbs, Elsevier, Amsterdam, p. 38 (1993)).

A third commonly used plant growth retardant for bulb plants is ethephon ((2-chloroethyl) phosphonic acid). Ethephon is known commercially as Ethrel®, Florel® or Cerone®. Ethephon has been found to control height reduction in lilies, hyacinths, daffodils and tulips and may be applied to these plants as a foliage spray or via a soil drench. Since ethephon releases ethylene, physiological disorders caused by ethylene exposure can result from the use of ethephon. For example, ethephon is known to cause flower abortion in some plants such as the tulip.

Although ethylene is known to inhibit stem elongation in some bulbous plants, the inventors of the present invention have unexpectedly discovered that an ACC synthase inhibitor, which inhibits the production of ethylene in plants, and is sold commercially as a cut flower preservative, can also be used to inhibit stem elongation in bulbous plants.

SUMMARY OF THE INVENTION

The present invention is directed to a process of inhibiting stem elongation in ornamental flowering bulbous plants and cut flowers therefrom. The process involves treating flowering bulbous plants and cut flowers from such plants with a sufficient amount of an ACC synthase inhibitor, such as AVG and AOA, preferably AVG, to inhibit stem elongation.

The ACC synthase inhibitor can be administered to bulb plants in the form of a solid, semi-solid or as a solution. If administered as a solid, the amount of ACC synthase inhibitor delivered to the plant may be from about 5 to about 50 milligrams (mg)/plant. If administered as a solution, the concentration of ACC synthase inhibitor in the solution will depend upon how the solution is applied to the plant. If the solution is applied as a media drench or a pre-plant soak, the concentration of ACC synthase inhibitor may be from about 50 to about 1000 parts per million (ppm). If the solution is applied as a foliar spray, the concentration of ACC synthase inhibitor may be from about 50 to about 2000 ppm. If the solution is to be used as a cut flower vase solution or hydroponic solution, the concentration of the ACC synthase inhibitor may be from about 0.1 to about 100 ppm. If the solution is to be delivered to cut flowers by immersion in a pre-treatment solution, the concentration of the ACC synthase inhibitor may be from about 50 to about 2000 ppm. If the ACC synthase inhibitor is to be used in plant cell tissue culture, the concentration of the ACC synthase inhibitor in the solution, semi-solid or solid media may be from about 0.001 mg/L to about 100 mg/L.

DETAILED DESCRIPTION OF THE INVENTION

The present invention is directed to a process of inhibiting stem elongation in ornamental flowering bulbous plants and cut flowers therefrom. In accordance with the process of the present invention, ornamental flowering bulbous plants and cut flowers are treated with an effective amount of an ACC synthase inhibitor to inhibit stem elongation. The term "bulbous plant", as used herein, refers to plant species having specialized underground organs which store food and moisture, thereby allowing for seasonal growth and development. The term "flowering bulbous plant", as used herein, refers to an intact, whole flowering bulbous plant. A flowering bulbous plant may be in a pot or other type of container or in the ground and may be in natural or artificial media. As used herein, the term "media" refers to a natural or artificial substance, in solid, semi-solid or liquid form, that can be used to propagate a plant. Examples of suitable types of media that can be used in this invention include soil, artificial or soilless potting mix, water (hydroponics) and agar. The term "cut flowers" as used herein refers to flowers from a flowering bulbous plant that have been removed in some manner from the plant.

The varieties of ornamental flowering bulbous plants that can be treated according to the process of this invention include acidanthera, agapanthus, allium, alstroemeria, amaryllis, anemome, astilbe, begonia, caladium, canna, chionodoxa, convallaria, crocosmia (montebretia), crocus, cyclamen, dahlia, daffodil, endymion, eranthis, eremurus, freesia, fritillaria, gladiolus, hyacinth, iris, ixia, liatris, lily, muscari, nerine, ornithogalum, polianth, ranunculus, scira, triteleia, tulip and zantedeschia (calla Ely). The preferred ornamental flowering bulbous plants that can be treated according to the process of this invention are amaryllis, daffodil, dahlia, freesia, gladiolus, hyacinth, iris, lily and tulip.

Several ethylene biosynthesis inhibitors, such as AVG, AOA and polyamines, are known in the art. The ACC synthase inhibitors used in this invention are AVG and AOA, which were utilized in previous inventions detailed in U.S. Pat. Nos. 5,284,818 and 5,550,403. The preferred ACC synthase inhibitor is AVG.

AVG is a naturally-occurring L-amino acid that is produced as a secondary metabolite by a Streptomyces sp. and is purified as the hydrochloride salt The AVG molecule can also be chemically synthesized, using a low yielding, multi-step, non-chiral synthetic scheme. AOA is a non-chiral synthetic molecule.

Both AVG and AOA have been shown to be inhibitors of ACC synthase (Wang, C. Y., Baker, J. E., HortScience, 15(6):805–806 (1980), Yang, S. F., Hoffman, N. E., Ann. Rev. Plant Physiol., 35:155–89 (1984)). The concentration of AOA required to inhibit ACC synthase in a plant is typically higher than the concentration of AVG required (Ibid.). In plants, ACC synthase converts SAM to ACC which is then converted to ethylene. Ethylene is known to inhibit stem elongation and PGR products which produce ethylene are used for this purpose with some plant species. Therefore, in the present invention, it was surprising to discover that ACC synthase inhibitors, such as AVG or AOA, which inhibit the production of ethylene in a plant, could be used to prevent stem elongation in bulbous plants.

For use in the process of this invention in cut bulb flowers, the ACC synthase inhibitor may be administered to cut flower stems alone or in combination with other ingredients, such as one or more sugars and/or one or more antimicrobial agents. Sugars provide a source of energy to the plant. Antimicrobial agents are believed to prevent clogging of the vascular system of cut plants caused by microbial growth. For example, a dry, solid cut flower preservative, marketed under the tradename Florish®, contains AVG or AOA, a sugar, glycoside, or a mixture thereof, aluminum sulfate, and an antimicrobial agent. Florish® may also contain a non-ionic and/or anionic surfactant to increase the uptake of the ACC synthase inhibitor into the plant, as well as a clarifying agent. Florish® contains from about 0.05 parts by weight to about 2 parts by weight of an ACC synthase inhibitor. Florish® is available as a dry, solid formulation, a complete description of which is provided in U.S. Pat. No. 5,284,818, incorporated herein by reference, or as a liquid concentrate, Florish® LC, a complete description of which is provided in U.S. Pat. No. 5,550,403, also incorporated herein by reference.

Florish® is different from other commonly used flower preservatives because it contains an ACC synthase inhibitor such as AVG or AOA in a stable powder formulation. Cut flower preservative formulations taught in the prior art include a sugar which provides an energy source for the cut flowers, an antimicrobial agent and inorganic salts. A review of the common ingredients of cut flower preservative formulations is provided by Halevy, A. H., Mayak, S., Horticultural Reviews, 3:59–143 (1981). Examples of commonly-available conventional cut flower preservatives include those sold under the trademarks Floralife®, Chrysal® and Oasis®.

The ACC synthase inhibitor may be administered to the cut flowers of bulb plants in the form of a solution. The solution is prepared by dissolving the ACC synthase inhibitor or the cut flower formulation containing the ACC synthase inhibitor in tap or distilled water. If the ACC synthase inhibitor is to be continuously delivered by uptake of a cut flower vase solution through the cut stems, the concentration of the ACC synthase inhibitor in the solution may be from about 5 to about 100 ppm, preferably from about 25 to about 75 ppm. If the ACC synthase inhibitor is to be delivered to the cut flowers by immersion of the cut stems in a treatment solution for a short treatment time lasting from about 1 about 72 hours, then the concentration of the ACC synthase inhibitor in the solution may be from about 50 to about 2000 ppm, preferably from about 500 to about 1000 ppm.

The ACC synthase inhibitor also may be applied to the cut flowers of bulb plants, either prior to harvest or post-harvest, as a foliar spray. When applied as a foliar spray, the concentration of AVG in the spray may be from about 50 to about 2000 ppm, preferably from about 100 to about 500 ppm. When applied as a foliar spray, the spray solution may also contain a surfactant, such as non-ionic and anionic surfactants, preferably an organosilicone surfactant, such as Silwet L-77®, which is available from OSi Specialties, Inc. Danbury, Conn. The concentration of organosilicone surfactant that can be used in the foliar spray is from about 0.025 to about 0.25% (v/v), preferably from about 0.05 to about 0.20% (v/v). Additionally, cut flowers can be treated with a combination of these solutions, such as with a cut flower vase solution and a foliar spray.

The ACC synthase inhibitor may be administered to flowering bulb plants in several different forms. In one aspect, the inhibitor may be administered to a flowering bulb plant in the form of a solid. For example, the inhibitor may be administered as a powder to the foliage and media, such as to the soil of a plant. After application of the powder to the plant, it is preferred that the plant be watered to facilitate uptake of the inhibitor into the cellular tissues of the plant However, if the media being used for propagation of the plant is water, such as in a hydroponics system, additional watering is not necessary. When the inhibitor is administered to a plant in the form of a solid, the amount of the ACC synthase inhibitor applied to the plant may be from about 5 to about 50 mg per plant in a solid formulation in which the concentration of the ACC synthase inhibitor is preferably from about 0.5% to about 95%.

In a second aspect, the ACC synthase inhibitor may be administered to flowering bulb plants in the form of a solution. The solution is prepared by dissolving the inhibitor in water, either tap or distilled. The solution containing the inhibitor can be used as a pre-plant soak of the bulb or applied to the flowering plants by a media drench or foliar spray. If the inhibitor is to be delivered in the solution as a pre-plant soak of the bulb, then the concentration of the inhibitor in the solution may be from about 50 to about 1000 ppm, preferably from about 100 to about 500 ppm. If the ACC synthase inhibitor is to be delivered to flowering bulbous plants by media drench, its concentration in the drench may be from about 50 to about 1000 ppm, preferably from about 250 to about 500 ppm. If the inhibitor is to be delivered as a foliar spray to flowering bulbous plants, its concentration in the spray may be from about 50 to about 2000 ppm, preferably from about 750 to about 1500 ppm.

Also, when the inhibitor is delivered as a foliar spray, the foliar spray may contain a surfactant, such as nonionic and anionic surfactants, preferably an organosilicone surfactant, such as Silwet L-77®. The concentration of organosilicone surfactant that can be used in the foliar spray is from about 0.025 to about 0.25% (v/v), preferably from about 0.050 to about 0.20% (v/v).

In a third aspect, the ACC synthase inhibitor may be administered to flowering bulb plants being cultivated in plant cell tissue culture containing a media which may be in the form of a solution, solid or semi-solid. The concentration of the ACC synthase inhibitor in the solution, semi-solid or solid media may be from about 0.001 mg/L to about 100 mg/L.

In addition to inhibiting stem elongation in flowering bulb plants, the process of the present invention can slow flower opening, reduce petal abscission, maintain flower form and extend overall vase life in certain cut bulb flowers such as the tulip.

The following Examples illustrate particular embodiments of the present invention with respect to tulips. Commercially, tulips are the major flowering ornamental bulb plant, with approximately 9000 hectares in production worldwide (De Hertogh, A. and M. Le Nard, eds., The Physiology of Flower Bulbs, Elsevier, Amsterdam, p. 660 (1993)). The stems of cut tulips continue to elongate after harvest and excessive growth is considered an undesirable and unattractive trait (Ibid.). Height control of potted tulips is important Plant growth retardants are used to reduce overall plant height by reducing stem elongation, thereby producing marketable compact plants. While the examples illustrate the invention with respect to tulips, the examples are not limiting of the specification in any way.

EXAMPLES

Example 1:

Cut Flower Stem Elongation Experiments using Florish®

Commercially-available cut tulips were obtained from growers or wholesalers. The tulip stems were recut under water and placed in vases of various treatment solutions. Treatment solutions included water, conventional cut flower preservatives which do not contain an ACC synthase inhibitor (Floralife® and Chrysal®) and Florish® (a cut flower preservative which includes an ACC synthase inhibitor). Once all stems were placed in vases, the length of the terminal internode was measured and recorded for each stem. The vases were held under fluorescent lighting at about 22°–24° C. After either 6 or 7 days, the terminal internode was re-measured.

Results Experiment #1

The tulip varieties used were 'Lustige Witwe' and 'Don Quichotte'. Eighteen cut flower stems of the cultivar 'Lustige Witwe' were recut underwater and placed into vases containing either local municipal tap water (6 stems), Floralife® (6 stems), or Florish® (6 stems). Six cut flower stems of the cultivar 'Don Quichotte' were recut underwater and placed into vases containing either local municipal tap water (2 stems), Floralife® (2 stems), or Florish® (2 stems). Solutions of these products were prepared according to label directions using local municipal tap water. Terminal internode length was measured for each stem at the beginning of the experiment and again after six days. The results are shown in Tables 1 and 2. An analysis of variance was conducted, and means were statistically separated using Duncan's Multiple Range Test. Means with common letter designations are not significantly different at p=0.05.

TABLE 1

Elongation of Terminal Internode
Cultivar: 'LUSTIGE WITWE'

| Treatment | Mean Elongation centimeters (cm) | Mean % Initial Length |
| --- | --- | --- |
| Water | 1.9 b | 119.5 b |
| Floralife ® | 8.2 a | 191.2 a |
| Florish ® | 2.4 b | 124.2 b |

TABLE 2

Elongation of Terminal Internode
Cultivar: 'DON QUICHOTTE'

| Treatment | Mean Elongation (cm) | Mean % Initial Length |
| --- | --- | --- |
| Water | 3.5 b | 171.0 a |
| Floralife ® | 5.5 a | 177.5 a |
| Florish ® | 3.5 b | 173.5 a |

The terminal internode of stems of 'Lustige Witwe' held in Floralife® grew about 6 cm longer than those held in Florish® or water over a 7 day period. Floralife® increased stem elongation beyond water or Florish® when expressed as centimeters increased or percent initial length. The terminal internode of stems of 'Don Quichotte' held in Floralife® grew more than those held in water or Florish® over a 7 day period. However, when expressed as a percentage of initial length, the difference was not statistically significant.

Experiment #2

Twenty cut flower stems of each of the cultivars 'Blenda' and 'Yokohama' were recut underwater and placed into vases containing either local municipal tap water (5 stems), Floralife® (5 stems), Chrysal® (5 stems), or Florish® (5 stems). Solutions of these products were prepared according to label directions using local municipal tap water. Terminal internode length was measured for each stem at the beginning of the experiment and again after six days. The results are shown in Tables 3 and 4. An analysis of variance was conducted, and means were statistically separated using Duncan's Multiple Range Test. Means with common letter designations are not significantly different at p=0.05.

TABLE 3

Elongation of Terminal Internode
Cultivar: 'BLENDA'

| Treatment | Mean Elongation (cm) | Mean % Initial Length |
| --- | --- | --- |
| Water | 1.4 c | 119.6 c |
| Floralife ® | 7.6 a | 181.6 a |
| Chrysal ® | 7.5 a | 185.4 a |
| Florish ® | 3.6 b | 141.4 b |

TABLE 4

Elongation of Terminal Internode
Cultivar: 'YOKOHAMA'

| Treatment | Mean Elongation (cm) | Mean % Initial Length |
| --- | --- | --- |
| Water | 1.2 b | 116.6 b |
| Floralife ® | 2.2 a | 128.2 a |
| Chrysal ® | 2.2 a | 129.2 a |
| Florish ® | 1.3 b | 116.6 b |

The terminal internode of stems of 'Blenda' and 'Yokohama' tulips held in Chrysal® or Floralife® solutions grew significantly more (longer) than those in Florish® or water.

The results in experiments #1 and #2 demonstrate that the continued growth of cut tulip stems is a significant problem. These results show that the Florish® solution, which contains an ACC synthase inhibitor, is able to reduce stem elongation in these plants.

Example 2
Cut Flower Vase Life Studies Using Florish®

Commercially-available cut tulips were obtained from a grower or wholesaler. Upon receipt, the cut flower stems were recut underwater and twelve stems of each cultivar ('Lucky Stripe', an unidentified white cultivar, and an unidentified yellow cultivar) were placed into each of the treatment solutions. Treatment solutions included local municipal tap water (12 stems), Floralife® (12 stems), and Florish® (12 stems). Solutions of these products were prepared according to label directions using local municipal tap water. The vases were held under fluorescent lighting at about 22°–24° C. The flowers were evaluated on a daily basis for viability. Results are presented in Tables 5, 6 and 7. An analysis of variance was conducted, and means were statistically separated using Duncan's Multiple Range Test. Means with common letter designations are not significantly different at p=0.05.

TABLE 5

Average Vase Life
Cultivar: 'LUCKY STRIKE'

| Treatment | Average Vase Life (Days) |
|---|---|
| Water | 7.5 b |
| Floralife ® | 8.4 ab |
| Florish ® | 8.7 a |

TABLE 6

Average Vase Life
Cultivar: 'Unidentified white tulip'

| Treatment | Average Vase Life (Days) |
|---|---|
| Water | 7.3 c |
| Floralife ® | 8.0 b |
| Florish ® | 8.6 a |

TABLE 7

Average Vase Life
Cultivar: 'Unidentified yellow tulip'

| Treatment | Average Vase Life (Days) |
|---|---|
| Water | 9.2 b |
| Floralife ® | 9.6 b |
| Florish ® | 10.4 a |

The results in this example demonstrate that Florish® cut flower preservative, which contains an inhibitor of ACC synthase, extends the vase life of cut tulips in comparison to a conventional cut flower preservative and tap water.

Therefore, as shown in Examples 1 and 2, Florish®, which contains an ACC synthase inhibitor, can effectively inhibit excessive stem elongation and increase overall vase life of cut tulips.

Example 3
Potted Tulip Experiments Using AVG-Containing Solutions

Potted tulips were acquired prior to application of PGR's by a commercial grower. No growth retardants had been applied to the plants prior to receipt. Foliar spray or media drench applications were made to bulb plants of uniform height when the plant flower stems were 10–15 centimeters (cm) tall. Spray applications were made to runoff with solutions containing from about 500 to about 2000 ppm AVG and 0.1% Silwet L-77®. Drench solutions containing from about 50 to about 500 ppm AVG were applied at a rate of 100 milliliters (mls) per 6 inch (15 cm) diameter pot. Plants were grown under greenhouse conditions for two weeks after applications were made. Stem length was recorded at various times.

Experiment #1

The potted tulip varieties used were 'Merry Christmas' and 'Christmas Marvel'. These potted plants were each treated with water containing 0.1% Silwet L-77 ®, 500 ppm, 1000 ppm, 1500 ppm or 2000 ppm AVG solution applied as a foliar spray when the plant flower stems were 10–15 cm tall. For each treatment, 3 pots containing 3 bulbs per pot were tested with each variety. Stem length was measured at 7 and 14 days after application of the spray to the plants. The results are shown in Tables 8 and 9. An analysis of variance was conducted, and means were statistically separated using Duncan's Multiple Range Test. Means with common letter designations are not significantly different at p=0.05.

TABLE 8

Cultivar: 'CHRISTMAS MARVEL'

| | Stem Length (cm) |
|---|---|
| Day 7 | |
| Control | 23.2 a |
| 500 ppm AVG foliar spray | 21.1 ab |
| 1000 ppm AVG foliar spray | 16.2 b |
| 1500 ppm AVG foliar spray | 19.8 ab |
| 2000 ppm AVG foliar spray | 18.9 ab |
| Day 14 | |
| Control | 30.0 a |
| 500 ppm AVG foliar spray | 26.7 ab |
| 1000 ppm AVG foliar spray | 25.6 b |
| 1500 ppm AVG foliar spray | 26.2 b |
| 2000 ppm AVG foliar spray | 25.1 b |

TABLE 9

CULTIVAR: 'MERRY CHRISTMAS'

| | Stem Length (cm) |
|---|---|
| Day 7 | |
| Control | 25.5 a |
| 500 ppm AVG foliar spray | 24.5 a |
| 1000 ppm AVG foliar spray | 22.1 b |
| 1500 ppm AVG foliar spray | 22.2 b |
| 2000 ppm AVG foliar spray | 20.8 b |
| Day 14 | |
| Control | 29.6 a |
| 500 ppm AVG foliar spray | 28.3 ab |
| 1000 ppm AVG foliar spray | 26.0 bc |
| 1500 ppm AVG foliar spray | 27.1 abc |
| 2000 ppm AVG foliar spray | 23.8 c |

The results in Tables 8 and 9 show that AVG causes significant stem length reduction in both 'Christmas Marvel' and 'Merry Christmas.' Rates of 1000–2000 ppm reduced stem lengths of both varieties significantly more than the controls at 14 days.

Experiment #2

The potted tulip varieties used were 'Merry Christmas' and 'Christmas Marvel'. These varieties were each treated with water, 50 ppm, 100 ppm, 250 ppm or 500 ppm AVG solution applied as a media drench. For each treatment, 3 pots containing 3 bulbs per pot were tested for each variety. Stem length was measured for these plants 7 and 14 days after application of the media drench. Tables 10 and 1 show the mean stem length for the 'Merry Christmas' and 'Christmas Marvel' plants at days 7 and 14. An analysis of variance was conducted, and means were statistically separated using Duncan's Multiple Range Test. Means with common letter designations are not significantly different at p=0.05.

TABLE 10

CULTIVAR: 'MERRY CHRISTMAS'

| | Stem Length (cm) |
|---|---|
| Day 7 | |
| Control | 23.0 a |
| 50 ppm AVG media drench | 23.6 a |
| 100 ppm AVG media drench | 23.8 a |
| 250 ppm AVG media drench | 21.7 a |
| 500 ppm AVG media drench | 17.7 b |
| Day 14 | |
| Control | 25.7 a |
| 50 ppm AVG media drench | 27.6 a |
| 100 ppm AVG media drench | 26.7 a |
| 250 ppm AVG media drench | 25.5 a |
| 500 ppm AVG media drench | 20.1 b |

TABLE 11

CULTIVAR: 'MERRY CHRISTMAS'

| | Stem Length (cm) |
|---|---|
| Day 7 | |
| Control | 19.9 b |
| 50 ppm AVG media drench | 24.1 a |
| 100 ppm AVG media drench | 23.4 a |
| 250 ppm AVG media drench | 20.2 b |
| 500 ppm AVG media drench | 19.0 b |
| Day 14 | |
| Control | 24.5 ab |
| 50 ppm AVG media drench | 26.7 a |
| 100 ppm AVG media drench | 27.8 a |
| 250 ppm AVG media drench | 23.7 ab |
| 500 ppm AVG media drench | 22.0 b |

The results in Tables 10 and 11 show an inhibition of stem elongation in both varieties with a 250 and 500 ppm AVG treatment.

Experiment #3

The potted tulip varieties used were 'Christmas Marvel' and 'SnowStar.' These varieties were each treated with a 500 ppm AVG solution applied as a media drench or a 2000 ppm AVG solution applied as a foliar spray. For the 'Christmas Marvel' variety, 10 pots containing 3 bulbs per pot were used for 10 each treatment. For the 'Snowstar' variety, 10 pots containing 6 bulbs per pot were used for each treatment. For 'Christmas Marvel', stem length was measured 7 and 13 days after the application of the media drench or foliar spray. For 'Snowstar', stem length was measured 7 days after application of the media drench or foliar spray. The results are shown in Tables 12 and 13. An analysis of variance was conducted, and means were statistically separated using Duncan's Multiple Range Test. Means with common letter designations are not significantly different at p=0.05.

TABLE 12

CULTIVAR: 'CHRISTMAS MARVEL'

| | Stem Length (cm) |
|---|---|
| Day 7 | |
| Control | 24.8 a |
| 500 ppm AVG media drench | 20.0 b |
| 2000 ppm AVG foliar spray | 14.6 c |
| Day 13 | |
| Control | 33.2 a |
| 500 ppm AVG media drench | 27.5 b |
| 2000 ppm AVG foliar spray | 20.8 c |

TABLE 13

CULTIVAR: 'SNOWSTAR'

| Day 7 | Stem Length (cm) |
|---|---|
| Control | 36.9 a |
| 500 ppm AVG media drench | 36.1 a |
| 2000 ppm AVG foliar spray | 30.4 b |

The results in Table 12 show significant height reduction compared to controls for the 'Christmas Marvel' variety with both drench and spray applications. Spray application gave significantly better height control than the media drench. Flowering of treated plants was delayed. The results in Table 13 show significant height reduction compared to controls for the 'SnowStar' variety when treated with a foliar spray. The media drench treatment was not effective with this particular variety. However, it should be noted that the plant development was quite advanced at the time of AVG application (plant flower stems were 20–25 cm tall).

Experiment #4

The potted tulip variety used was 'Prominence'. This variety was treated with water or 500 ppm AVG solution applied as a media drench. For each treatment, 4 pots containing 6 bulbs per pot were tested. Stem length was measured 5 and 11 days after application of the media drench. For each treatment, 4 pots containing 6 bulbs per pot were tested. Table 14 shows the mean stem length of these plants. Means were statistically analyzed. An analysis of variance was conducted, and means were statistically separated using Duncan's Multiple Range Test. Means with common letter designations are not significantly different at p =0.05.

TABLE 14

CULTIVAR: 'PROMINENCE'

| | Stem Length (cm) |
|---|---|
| Day 5 | |
| Control | 23.5 a |
| 500 ppm AVG media drench | 19.2 b |
| Day 11 | |
| Control | 33.8 a |
| 500 ppm AVG media drench | 26.6 b |

The results in Table 14 shows that AVG causes a significant reduction in stem elongation compared to the controls.

Experiment #5

The potted tulip variety used was the dwarf variety 'Kareol.' This tulip variety was treated with water, 350 ppm or 500 ppm AVG solution applied as a media drench. For each treatment, 6 pots containing 6 bulbs per pot were tested. Stem length was measured 7 days after application of the media drench. For each treatment, 6 pots containing 6 bulbs per pot were tested. Table 15 shows the mean stem length of these plants. An analysis of variance was conducted, and means were statistically separated using Duncan's Multiple Range Test Means with common letter designations are not significantly different at p=0.05.

TABLE 15

CULTIVAR: 'KAREOL'

| Day 7 | Stem Length (cm) |
|---|---|
| Control | 20.8 a |
| 350 ppm AVG media drench | 20.1 a |
| 500 ppm AVG media drench | 20.3 a |

The results in Table 15 show slight numerical height reduction compared to controls. It should be noted that since 'Kareol' is a dwarf variety, dramatic effects of AVG on stem elongation would not be expected.

The results in experiments #1–#5 demonstrate that applications of an ACC synthase inhibitor such as AVG, as either a foliar spray or media drench, gave significant inhibition of stem growth to several varieties of potted tulips.

SUMMARY OF THE EXAMPLES

The above Examples demonstrate that an ACC synthase inhibitor, such as AVG or AOA, inhibits stem elongation in cut and potted tulip plants and cut flowers therefrom. The finding that an ACC synthase inhibitor could be used to inhibit stem elongation was surprising since ACC synthase inhibitors, such as AVG and AOA, are sold in cut flower preservatives and flower preservatives generally tend to exacerbate stem elongation. It was also unexpected to find that an ACC synthase inhibitor, which prevents the formation of ethylene, which reduces stem elongation in plants, could be used to inhibit stem elongation in bulbous plants. Finally, the above Examples also demonstrate that an ACC synthase inhibitor can be used to extend the vase life of cut flowers.

What is claimed is:

1. A process of inhibiting stem elongation in flowering bulbous plants comprising treating said bulbous plants with an effective amount of an ACC synthase inhibitor to inhibit stem elongation.

2. A process of inhibiting stem elongation in cut flowers from flowering bulbous plants comprising treating said bulbous plants with an effective amount of an ACC synthase inhibitor before the flower is cut to inhibit stem elongation.

3. A process according to claim 1 or claim 2, wherein the ACC synthase inhibitor is selected from the group consisting of aminoethoxyvinylglycine and aminooxyacetic acid.

4. A process according to claim 1 or claim 2, wherein the bulbous plant is acidanthera, agapanthus, allium, alstroemeria, amaryllis, anemome, astilbe, begonia, caladium, canna, chionodoxa, convallaria, crocosmia (montebretia), crocus, cyclamen, dahlia, daffodil, endymion, eranthis, eremurus, freesia, fritillaria, gladiolus, hyacinth, iris, ixia, liatris, lily, muscari, nerine, ornithogalum, polianth, ranunculus, scilla, triteleia, tulip or zantedeschia (calla lily).

5. A process according to claim 1 or claim 2, wherein the ACC synthase inhibitor is administered to the bulbous plants as a solid.

6. A process according to claim 5, wherein the solid contains from about 0.5 to about 95% ACC synthase inhibitor.

7. A process according to claim 1 or claim 2, wherein the ACC synthase inhibitor is administered to the bulbous plants by a media drench, by foliar spray, by cut flower vase solution, by cut flower pre-treatment solution, by hydroponics solution, by pre-plant soak of the bulb, or by a combination of these methods.

8. A process according to claim 7, wherein the media drench contains from about 50 to about 1000 ppm of an ACC synthase inhibitor, the foliar spray contains from about 50 to about 2000 ppm of an ACC synthase inhibitor, the cut flower vase solution contains from about 5 to about 100 ppm of an ACC synthase inhibitor, the pre-plant soak of the bulb contains from about 50 to about 1000 ppm of an ACC synthase inhibitor, the cut flower pre-treatment solution contains from about 50 to about 2000 ppm of an ACC synthase inhibitor, and the hydroponics solution contains from about 0.1 to about 10 ppm of an ACC synthase inhibitor.

9. A process according to claim 1 or claim 2, wherein the ACC synthase inhibitor is administered to the bulbous plants in plant cell tissue culture and the concentration of the ACC synthase inhibitor in the plant tissue culture is from about 0.001 mg/L to about 100 mg/L.

10. A process of extending the vase life of cut flowers from bulbous plants by inhibiting stem elongation comprising treating said cut flowers with an effective amount of an ACC synthase inhibitor to inhibit stem elongation.

* * * * *